United States Patent [19]

Rober

[11] 4,122,705

[45] Oct. 31, 1978

[54] O-RING INSPECTION APPARATUS

[75] Inventor: Herbert E. Rober, Roseville, Mich.

[73] Assignee: General Motors Corporation, Detroit, Mich.

[21] Appl. No.: 809,790

[22] Filed: Jun. 24, 1977

[51] Int. Cl.² .............................................. G01N 3/08
[52] U.S. Cl. ........................................ 73/794; 73/800; 73/832
[58] Field of Search ..................... 73/88 R, 95, 100, 99

[56] References Cited

U.S. PATENT DOCUMENTS

| 3,365,938 | 1/1968 | Matsushita et al. ..................... 73/95 |
| 3,447,361 | 6/1969 | Schmitt ............................... 73/88 R |

Primary Examiner—Jerry W. Myracle
Attorney, Agent, or Firm—Warren D. Hill

[57] ABSTRACT

A pair of mandrels crossing at a right angle are moved into the center of an O-ring and then spread apart to stretch the O-ring around the mandrels to secure it and to form it into a twisted path. The mandrels are rotated to drive the O-ring through the twisted path so that the angular orientation of any given cross section of the O-ring changes as it advances around the path. An optical measurement apparatus senses cross section diameter of the O-ring at several locations. A support for one of the mandrels accommodates a load cell to measure the force developed by stretching the O-ring to provide a measure of O-ring elasticity.

2 Claims, 4 Drawing Figures

O-RING INSPECTION APPARATUS

This invention relates to a method and apparatus for inspecting O-rings, and particularly for measuring the elasticity thereof.

In the past it has been impractical to thoroughly inspect all the O-rings used in a large scale assembly operation. When the O-rings are used, for example, as seals in a hydraulic mechanism, the mechanism is tested after assembly for leakage. For each leakage that occurs due to a defective O-ring, the mechanism must be disassembled for O-ring replacement. That expensive repair procedure can be minimized or eliminated by inspecting each O-ring before its use. It is a common practice to use visual inspection of individual O-rings, however, this is time consuming and is generally applied only to selected samples.

Moreover faults in elastomeric seals may manifest only after extended operation in a mechanism. Such faults are generally attributed to overall or localized softness caused by improper curing of the material or a non-uniform material mixture. To control the quality of such seals, it has been the practice to test hardness of selected samples by standard durometer measurements. It is not practical to apply that measurement to every point on the surface of an O-ring or to so inspect large quantities of O-rings. It has been found, however, that the elasticity of an O-ring is dependent on the degree of cure of the material and provides a simple measurement of all areas of the O-ring to predict how well the O-ring will perform as a seal.

It is therefore a general object of the invention to provide a test apparatus for quality of O-rings responsive to all portions of the O-ring and practical for testing large quantities of O-rings.

It is a further object to provide an apparatus for quickly and automatically gripping an O-ring, stretching it and measuring the resulting force developed on the O-ring to obtain a measure of its elasticity.

The invention is carried out by providing an inspection machine having a pair of mandrels movable along one axis for insertion into an O-ring having means for moving at least one of the mandrels laterally of that axis to stretch the O-ring a predetermined amount, a motor for driving the mandrels to move the O-ring through a twisted path, and a transducer for measuring the force exerted on one of the mandrels by the stretched O-ring to obtain a measure of the O-ring elasticity.

The above and other advantages will be made more apparent from the following specification taken in conjunction with the accompanying drawings wherein like reference numerals refer to like parts and wherein.

Figure 1:
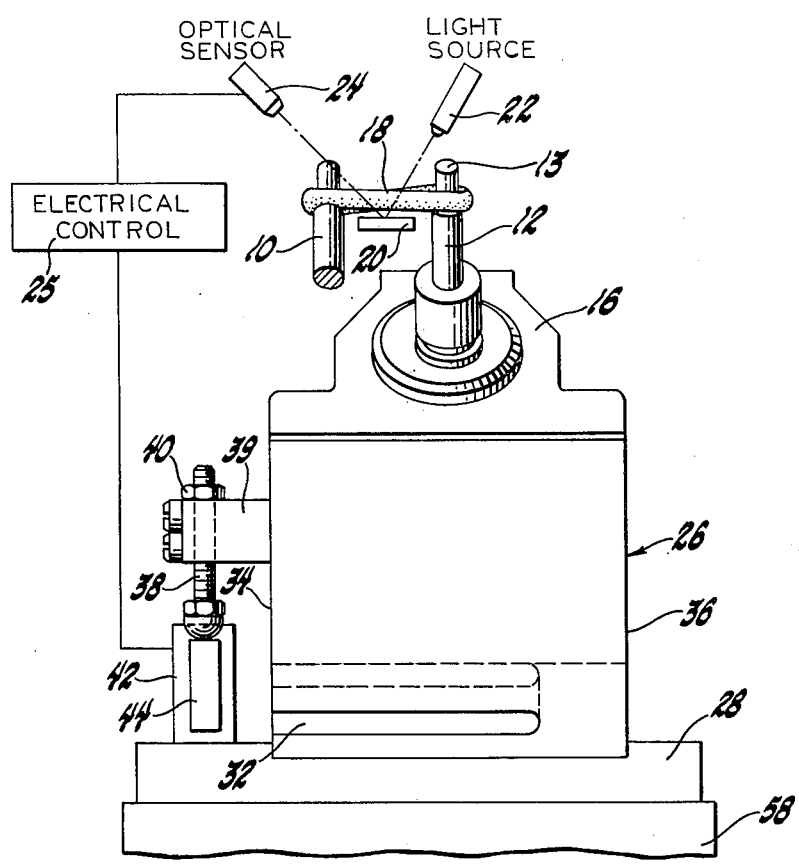
FIG. 1 is a front elevation of a portion of the O-ring inspection apparatus and particularly including the system for gripping the O-ring and measuring its elasticity according to the invention.

The drawings depict the principle of operation of the subject invention and includes a pair of spaced arbors or mandrels 10 and 12 rotatably carried by spindles 14 and 16, respectively. The mandrel 10 is rotatably driven by a motor 66. The mandrels, although in separate planes, are crossed at approximately right angles in order to securely grip an O-ring 18 which is stretched around the mandrels. Because of the angular disposition of the mandrels, the O-ring is contorted into a twisted path and since the mandrel 10 is rotating, the O-ring progressively moves through that twisted path. Because of the twist, any given cross-sectional element of the O-ring changes its angular disposition as it advances around the twisted path.

In order to optically inspect the surface of the O-ring 18 for dimensional anomalies in the same test procedure as the elasticity measurement, there is provided a mirror 20 (FIG. 1) adjacent one side of the O-ring, a light source 22 to illuminate the mirror, and an optical sensor 24 for monitoring the cross-section of the O-ring as it is driven through its twisted path. Electrical signals from the sensor 24 are processed by an electrical control 25 including a microprocessor, for example. The details of the optical inspection system are further revealed in the U.S. patent application Ser. No. 726,776 now U.S. Pat. No. 4,062,633 of Stapleton et al.

Figure 2:
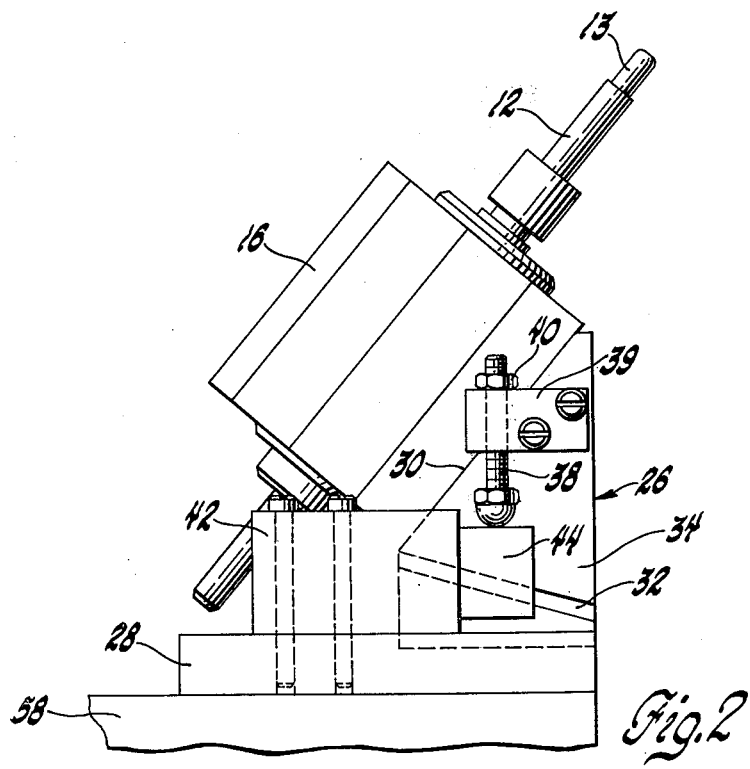
FIG. 2 is a side elevation of the portion of the apparatus of FIG. 1.

As shown in FIGS. 1 and 2, the spindle 16 is supported by an aluminum support block 26 which in turn is mounted on a base 28. The base plate is carried by a carriage 58. An upper face 30 of the support block 26 carries the spindle 16 and is inclined at an angle to establish the desired attitude of the spindle 12. The support block 26 is a generally rigid structure except for a slot 32 formed in one side face 34 of the block nearest the mandrel 10, the slot extending most of the way through the block but stopping short of the opposite side face 36 to define a region of reduced cross section between the slot 32 and the side face 36 joining upper and lower rigid block portions of large cross section. The plate of the slot is at such an angle that a line can be drawn from the O-ring gripping portion 13 of the mandrel 12 perpendicular to the plane of the slot. Thus the force developed in an O-ring 18 stretched between mandrels 10 and 12 tends to flex the block 26 at the reduced area portion to slightly deflect the upper portion of the block 26. An arm 39 extending laterally from the side face 34 of the upper portion of the block 26 holds a vertically depending threadedly adjustable bolt-like pin 38 secured by a locknut 40.

A beam type load cell 42 is attached to the base plate 28 beneath the arm 39 with its beam 44 in contact with lower end of the pin 38. The load cell is, for example, type MB-10 manufactured by Interface, Inc. of Scottsdale, Arizona, having a load range of 0 to 10 pounds and a maximum beam deflection of 0.005 inch. The electrical output signal voltage of the load cell is proportional to the force applied to the beam by the pin 38. The signal is fed to the electrical control 25 for evaluation. When an O-ring of a given size is stretched between the mandrels 10, 12 to a predetermined elongation, the force developed within the O-ring is a measure of the O-ring elasticity. The force tends to deflect the upper portion of the support block 26 causing the pin 38 to bear down on the load beam 44 with a force proportional to the O-ring force, so that a proportional electrical signal is produced by the load cell.

Figure 3:
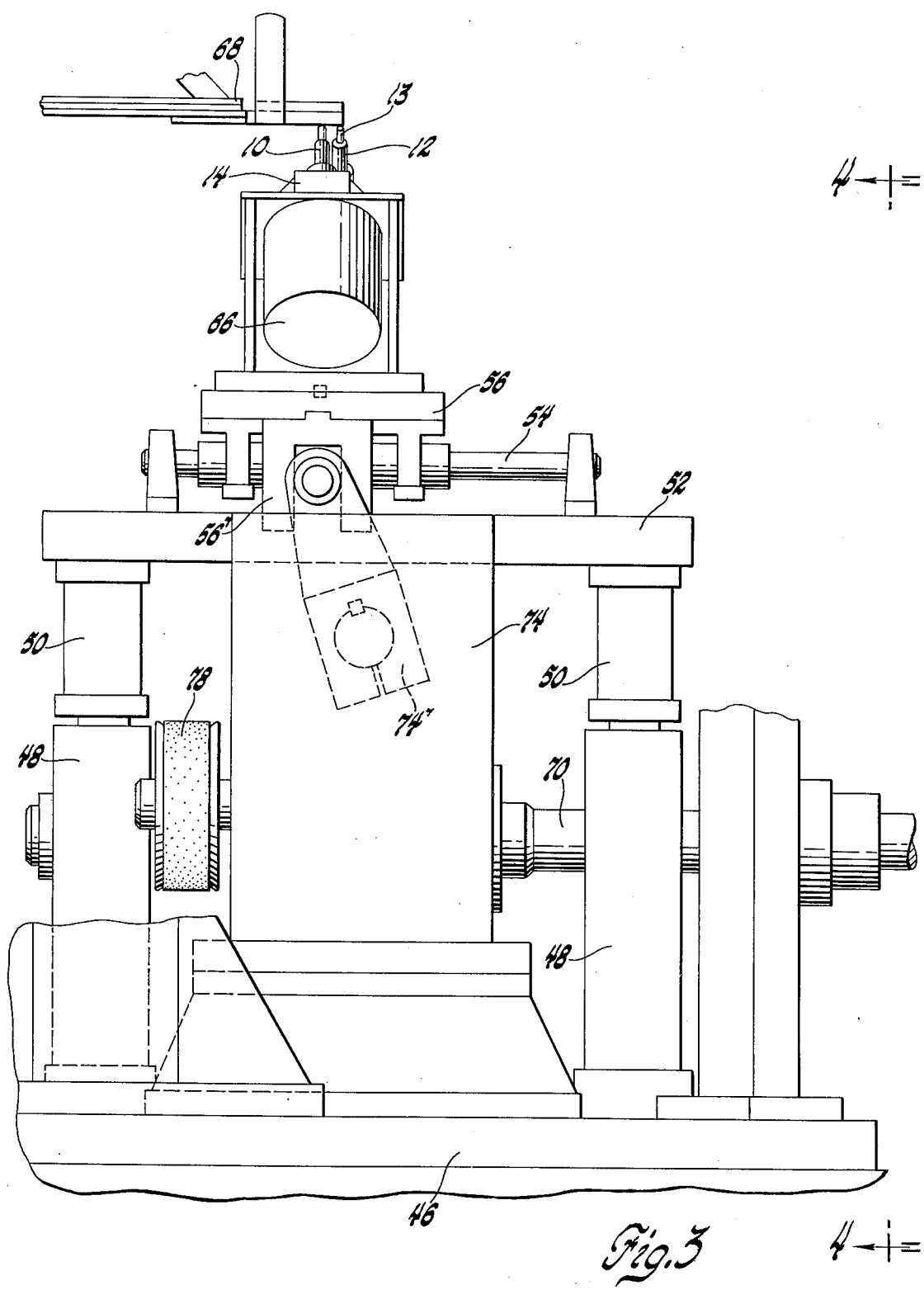
FIG. 3 is a front elevation of the O-ring inspection apparatus with the optical elements omitted.
Figure 4:
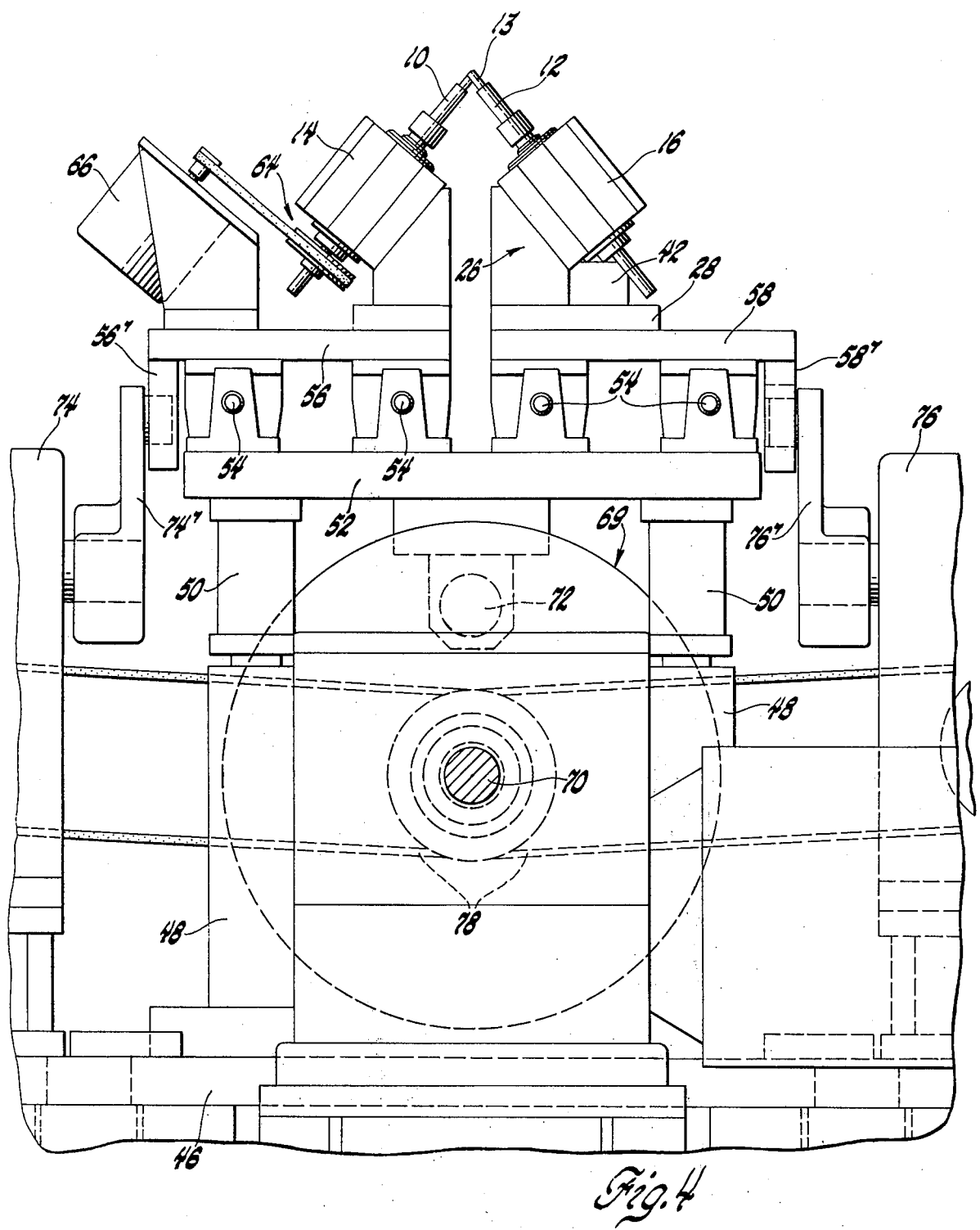
FIG. 4 is a side elevational view of the apparatus taken along lines 4—4 of FIG. 3.

FIGS. 3 and 4 depict the machine for handling the O-rings and presenting them to the optical measuring apparatus which is omitted in these views. The machine includes a base 46, columns 48 carrying telescoping vertical extensions 50 guided in ball bearings. The extensions 50 support a horizontal platform 52. This carries a plurality of horizontal rails 54. A pair of carriages 56 and 58 are slidably carried on the rails for horizontal movement. The carriages 56 and 58 support spindles 14 and 16, respectively, in which the mandrels 10 and 12 respectively are mounted. The mandrel 10 is driven through a belt and pulley arrangement 64 by a motor 66. A chute or tray 68 above the mandrels feeds O-rings to a position aligned with the center of the mandrel assembly. Beneath the platform 52 is a rotating cam assembly 69 having a cam, not shown, driven through a shaft 70 by a motor, not shown. A cam follower 72 depends from the under surface of the platform 52 and engages the cam for control thereby so that as the cam is rotated by the shaft 70, the platform 52 and therefore the mandrels 10 and 12 are raised and lowered according to a prescribed program. Roller oscillators 74 and 76 on either side of the cam assembly are driven by timing belts 78 in synchronism with the rotation of the cam. The mechanical outputs of the roller oscillators are arms 74' and 76' which engage side yokes 56' and 58' on the carriages 56 and 58, respectively, so that the carriages are controlled in their horizontal movement according to preset programs in the roller oscillators 74 and 76.

In operation, an O-ring having, for example, an inner diameter of 0.549 inch and an outer diameter of 0.755 inch is fed along the tray 68 to a position above the mandrels 10 and 12. The cam assembly raises the platform 52½ inches to insert the mandrels into the center of the O-ring, then the arm 76' of the roller oscillator 76 shifts the carriage 58 to move the mandrel 12⅝ inches to the right thereby stretching the O-ring as well as twisting it and holding it in place as shown in FIG. 1. The motor 66 runs continuously so that the O-ring is being driven through its twisted path so long as it is engaged by the mandrels.

The movement of the mandrel 12 stretches the O-ring a predetermined amount and the force measurement is made by the load cell 42. The electrical control determines whether the force is within prescribed limits. If not, the O-ring is rejected forthwith. If the O-ring passes the elasticity test, the optical inspection ensures. The straight O-ring segments are then within the optical field of the sensor 24 and the images of the segments are measured. When the optical measurement which takes one second is complete, the arms 74' and 76' are simultaneously actuated to move the mandrel 12 to the right 1⅜ inches and to move the mandrel 10 to the right 2 inches so that the O-ring is moved to a tray, not shown, at an eject station for release by the mandrels. Then the platform 52 is lowered to its original position to withdraw the mandrels from the O-ring whereupon the roller oscillators 74 and 76 return the mandrels to their initial station. The ejected O-ring is then passed to a "reject" bin or "accept" bin by well known apparatus, not shown, which is controlled by the electrical control 25. The total machine cycle time for each O-ring is 3.6 seconds.

It will thus be seen that the apparatus of this invention provides means for automatically gripping an O-ring and rapidly testing its elasticity to obtain a measure of seal quality, the test being cooperative, if desired, with optical O-ring inspection incorporated in the same apparatus.

The embodiments of the invention in which an exclusive property or privilege is claimed are defined as follows:

1. An apparatus for dynamically measuring the elasticity of O-rings formed of elastomeric material comprising, a pair of spaced mandrels, each rotatably mounted in a support, the mandrels being crossed at an angle, means for presenting an O-ring to a position adjacent the mandrels with the O-ring axis aligned with the mandrels, means moving the mandrels generally along said axis for inserting the mandrels through the opening of the O-ring, means for moving at least one of the mandrels laterally with respect to the axis to move the mandrels apart a fixed distance whereby the O-ring is securely gripped and stretched to effect a predetermined elongation of the O-ring, means for rotating the mandrels to drive the O-ring through a path around the mandrels, and means effective while the O-ring is driven through the said path for measuring the force on one of the mandrel supports resulting from the force developed by the elongation of the O-ring whereby the measured force is a measure of the O-ring elasticity.

2. An apparatus for dynamically measuring the elasticity of O-rings formed of elastomeric material comprising, a pair of spaced mandrels, each rotatably mounted in a support, the mandrels being crossed at an angle, one of the supports including relatively rigid portions of large cross section joined by a relatively flexible portion of reduced cross section integral with the rigid portions, whereby deflection of the said one support occurs in response to a force applied between the mandrels, means for presenting an O-ring to a position adjacent the mandrels with the O-ring axis aligned with the mandrels, means moving the mandrels generally along said axis for inserting the mandrels through the opening of the O-ring, means for moving at least one of the mandrels laterally with respect to the axis to move the mandrels apart a fixed distance whereby the O-ring is securely gripped and stretched to effect a predetermined elongation of the O-ring, and sensor means for measuring the force on the said one mandrel support resulting from the force developed by the elongation of the O-ring comprising a sensor connected across the said rigid portions to measure the said force, and to produce an output signal in accordance therewith, whereby the measured force is a measure of the O-ring elasticity.

* * * * *